United States Patent [19]

Cripps

[11] 4,444,751

[45] Apr. 24, 1984

[54] NEUTRALIZING COMPOSITION FOR STING VENOMS

[75] Inventor: Raymond A. Cripps, Newport News, Va.

[73] Assignee: Vannguard of Hampton, Inc., Hampton, Va.

[21] Appl. No.: 301,631

[22] Filed: Sep. 14, 1981

[51] Int. Cl.$^3$ .............................................. A61K 37/48
[52] U.S. Cl. .................................... 424/94; 424/232; 424/230
[58] Field of Search .......................................... 424/94

[56] References Cited

U.S. PATENT DOCUMENTS

| | | |
|---|---|---|
| 2,917,433 | 12/1959 | Goldman . |
| 2,995,493 | 8/1961 | Douglas. |
| 3,003,917 | 10/1961 | Beiler. |
| 3,324,002 | 6/1967 | Antonides . |
| 3,627,875 | 12/1971 | Dremet . |
| 3,860,702 | 1/1975 | Buell . |
| 4,108,984 | 8/1978 | Sato . |

OTHER PUBLICATIONS

Velluz–Chem. Abst. vol. 32 (1938). p. 6333$^4$.
Kim et al–Chem. Abst. vol. 60 (1964) p. 12285c.
Tachibana–Chem. Abst. vol. 42 (1948) pp. 6413i & 6414a–c.
Cardoni et al.,–Chem. Abst. vol. 96, (1982) p. 117,215x.
Goodman L. S. and A. Gilman, E.D.S. *The Pharmacological Basis of Therapeutics*, 5th Ed. MacMillan Publishing Co., Inc. 1975, p. 958.

*Primary Examiner*—Sam Rosen
*Attorney, Agent, or Firm*—Armstrong, Nikaido, Marmelstein & Kubovcik

[57] ABSTRACT

A composition for neutralizing noxious plant and animal venoms. The composition comprises a proteolytic enzyme in combination with a carrier suitable for topical application to the skin. In a preferred embodiment the proteolytic enzyme is papainase and the composition also contains gallic acid which causes localized blood vessel constriction and restricts dispersal of the venom and methyl salicylate which increases the penetrant ability of the composition.

6 Claims, No Drawings

NEUTRALIZING COMPOSITION FOR STING VENOMS

BACKGROUND OF THE INVENTION

1. Field of the Invention

The present invention relates to an anti-venom composition and, particularly, to a topical preparation for the treatment of noxious stings of plant and animal origin.

2. Description of the Prior Art

Proteolytic enzymes such as alpha amylase, bromelains, deoxyribonuclease combined with fibrinolysin and papain are disclosed as being useful for relieving symptoms relating to episiotomy, in the debriding of open wounds and ulcers, and as anti-inflammatory agents for subdermal tissue lesions. The action of the enzymes is due to hydrolyzation of peptide bonds with subsequent denaturalization of the proteins that constitute the traumatized tissue.

It is also known that venoms of most stinging organisms are proteinaceous in whole or part.

SUMMARY OF THE INVENTION

The present invention is based on the discovery that proteolytic enzymes and, in particular, papainase, are effective in neutralizing toxicants introduced into the epidermis by stings, bites or the like.

According to the present invention, a composition for neutralizing sting venom of plant or animal origin comprises a proteolytic enzyme in combination with a carrier suitable for topical application to the skin.

In a preferred embodiment of the neutralizing composition according to the present invention, papain (papainase EC No. 3.4.4.10) is employed in combination with gallic acid and methyl salicylate.

DESCRIPTION OF PREFERRED EMBODIMENTS

Any of the known proteolytic enzymes including alpha amylase, bromelains, deoxyribonuclease and papain are believed to be useful as the active agent in the neutralizing composition for sting venoms according to the present invention. Papain (Papainase EC No. 3.4.4.10) has been found to be particularly useful as the active agent since it can be employed for treating sting venoms originating from a wide variety of plants and animals. Derivatives, such as salts, of the proteolytic enzymes which do not inhibit the active, i.e., neutralizing, properties of the enzymes can also be used in the composition.

The proteolytic enzyme (hereinafter: the active agent) can be employed in combination with virtually any carrier suitable for topical application to the skin. Such carriers include, for example, coconut oil, solutions of carboxyvinyl polymers and the like. Water can be conveniently employed as the carrier. If water is employed as the carrier, a demulcent such as sodium alginate (a hydrocolloid), is included in the composition to enable the active agent to remain suspended and thus to provide more uniform application to the skin.

The amount of the active agent employed in the composition is not particularly limited. The precise amounts employed depend upon numerous factors such as the nature of the sting venom, the particular carrier employed, desired viscosity, amount of the composition to be applied to the skin and the like. In a typical composition employing water as the carrier, about 0.5–2 grams of the active ingredient per 100 ml of the composition are employed.

The effectiveness of the proteolytic composition according to the invention can be further enhanced by including a small amount of gallic acid therein. Localized blood vessel constriction due to the action of the gallic acid on the smooth muscles of the capillary vessels helps to prevent the dispersal of the sting venom in the affected area. Thus, the gallic acid acts to promote rapid neutralization of the localized venom by the active agent. The gallic acid is employed in the neutralizing composition in an amount of about 1–5 percent based on the weight of the active agent in the composition.

In a further embodiment of the neutralization composition according to the present invention, methyl salicylate is included in the composition to increase the penetrant ability of the composition and to act as a counterirritant. The methyl salicylate is included in the composition in an amount of from about 1–5 percent based on the weight of the active agent in the composition. An excessive amount of the methyl salicylate can cause irritation. When water is employed as the carrier, the methyl salicylate is first dissolved in alcohol and the alcoholic solution is combined with the water.

The neutralization composition according to the present invention may also contain conventional antioxidants and preservatives such as, for example, methylparaben and sodium benzoate.

The neutralizing composition can be applied topically to the sting area by conventional means such as, for example, massaging a liberal amount of the composition with circular motion into the area of sting penetration from the periphery toward the center of the affected area.

The neutralizing compositions according to the invention, as noted above, are employed for neutralizing noxious plant and animal venoms. Compositions of the invention in which the active agent is papain are particularly useful in the treatment of jellyfish stings.

To illustrate the preparation of the composition of the invention, the following example is given. Unless indicated otherwise, amounts are by weight.

EXAMPLE

A solution in accordance with this invention may be prepared as follows:

0.750 gm. of papain (Papainase E.C. No. 3.4.4.10, Crude powder, Type 11, Sigma Chemical Co.) are added to 100 ml. of distilled water and thoroughly mixed. 1 gm. of algin (sodium alginate) is slowly added while gently stirring. To this colloidal mixture are added 5 ml. of gallic acid (standard solution) and 1 ml. of methyl salicylate (standard solution) to produce a pH of between 5 and 5.5. The resultant solution is thoroughly mixed.

Standard Solutions:
(a) 1 gm gallic acid to 87 ml. distilled water
(b) 1 vol. methyl salicylate to 7 vol. 70% ethyl alcohol Although the present invention has been described in conjunction with certain preferred embodiments, the invention is not limited thereto but, instead, includes all those embodiments within the spirit and scope of the appended claims.

I claim:

1. A composition for neutralizing sting venom of plant or animal origin comprising a sting venom neutralization amount of papainase, gallic acid and methyl salicylate, and a carrier suitable for topical application to the skin.

2. The composition of claim 1 wherein the carrier is water.

3. The composition of claim 1 wherein the gallic acid and methyl salicylate are each present in an amount of 1 to 5% based on the weight of the papainase.

4. A method for neutralizing sting venom of plant or animal origin comprising applying topically to the skin a composition comprising a sting venom neutralization amount of papainase, gallic acid and methyl salicylate, and a carrier suitable for topical application to the skin.

5. The method of claim 4 wherein the carrier is water.

6. The method of claim 4 wherein the gallic acid and methyl salicylate are each present in an amount of 1 to 5% based on the weight of the papainase.

* * * * *